United States Patent [19]

Miwa et al.

[11] Patent Number: 4,940,332
[45] Date of Patent: Jul. 10, 1990

[54] FLUORESCENT ANALYSIS APPARATUS

[75] Inventors: Harufumi Miwa, Kawasaki; Minoru Kashiwada; Yoshimasa Yahagi, both of Kawaguchi, all of Japan

[73] Assignee: Ajinomoto Co., Inc., Tokyo, Japan

[21] Appl. No.: 228,588

[22] Filed: Aug. 5, 1988

[30] Foreign Application Priority Data

Aug. 5, 1987 [JP] Japan ................................ 62-194314

[51] Int. Cl.⁵ ............................................. G01N 21/64
[52] U.S. Cl. .................................. 356/417; 250/458.1; 435/291; 422/64; 436/172
[58] Field of Search ................... 356/317, 318, 417; 250/458.1, 459.1, 461.1, 461.2; 435/291; 422/63, 64, 65, 67, 68; 436/45, 165, 172

[56] References Cited

U.S. PATENT DOCUMENTS

| Re. 28,801 | 5/1976 | Acker et al. | 435/291 |
| 3,837,745 | 9/1974 | Acker et al. | 435/291 |
| 3,877,817 | 4/1975 | Ralston | 422/68 |
| 4,698,308 | 10/1987 | Ikeda | 435/291 |
| 4,778,763 | 10/1988 | Makiguchi et al. | 250/459.1 |

Primary Examiner—F. L. Evans
Attorney, Agent, or Firm—Oblon, Spivak, McClelland, Maier & Neustadt

[57] ABSTRACT

An apparatus for measuring the presence of microorganisms using fluorescent substances. A number of samples are measured continuously by enclosing the entire reacting and measurement sections within a thermostatically controlled enclosure. A number of samples are placed in containers with reactive liquids and placed in the reacting section of the enclosure. After the specified time within the enclosure, the container is rotated to the measuring section. The remaining liquid is filtered and activating light shined therethrough. The fluorescent light given off is measured to indicate the presence of microorganisms.

9 Claims, 4 Drawing Sheets

FLUORESCENT ANALYSIS APPARATUS

BACKGROUND OF THE INVENTION

1. Field of the Invention

The present invention relates generally to an apparatus for a fluorescent analysis for the presence of microorganisms and more particularly to an apparatus for a fluorescent analysis where a thermostatically controlled enclosure contains all the apparatus for the reaction and for measurement.

2. Discussion of the Background

A common method of testing for the presence of microorganisms in food is the process of causing microorganisms to decompose a fluorescent substrate to yield fluorescent substances. For example, a sample of soup and a reactive liquid containing $10^{-3}$ mole of 4-methylumbelliferil phosphate, a fluorescent substrate, are mixed in a test tube and reacted for two hours in a reacting tank at a temperature of 40° C. After impurities are separated by a centrifuge, the amount of fluorescent substance formed is measured.

While methods such as this produce adequate results, it is preferable to examine numerous samples quickly and accurately. In the past, the step of reacting the microorganisms with the fluorescent substrate and the step of measuring the formed fluorescent substance were done independently in different apparatuses. The operator had to move between the two test sites and move the test tubes, which wasted time. In addition, the reacting and measuring operations were not carried out continuously, so that it was difficult to effectively deal with a large number of samples. Furthermore, this situation did not lend itself to an automated system.

SUMMARY OF THE INVENTION

Accordingly, one object of this invention is to provide a novel fluorescent analysis apparatus which performs the reacting and measuring test continuously.

Another object of this invention is to provide a fluorescent analysis apparatus which performs the reacting and measuring tests on a series of samples at one time.

Another object of this invention is to provide a fluorescent analysis apparatus where the entire apparatus is enclosed within a thermostatically controlled enclosure.

A still further object of this invention is to provide a fluorescent analysis apparatus which lends itself to automation.

These and other objects of the inventions are achieved by providing a thermostatically controlled enclosure containing a measuring apparatus and a reacting board. The reacting board carries a large number of samples in a circle and rotates the samples as necessary to a measuring station. Each sample is automatically filtered when it reaches the measuring station. By maintaining all of the equipment within a single enclosure the temperature may be kept constant at the best reaction level.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
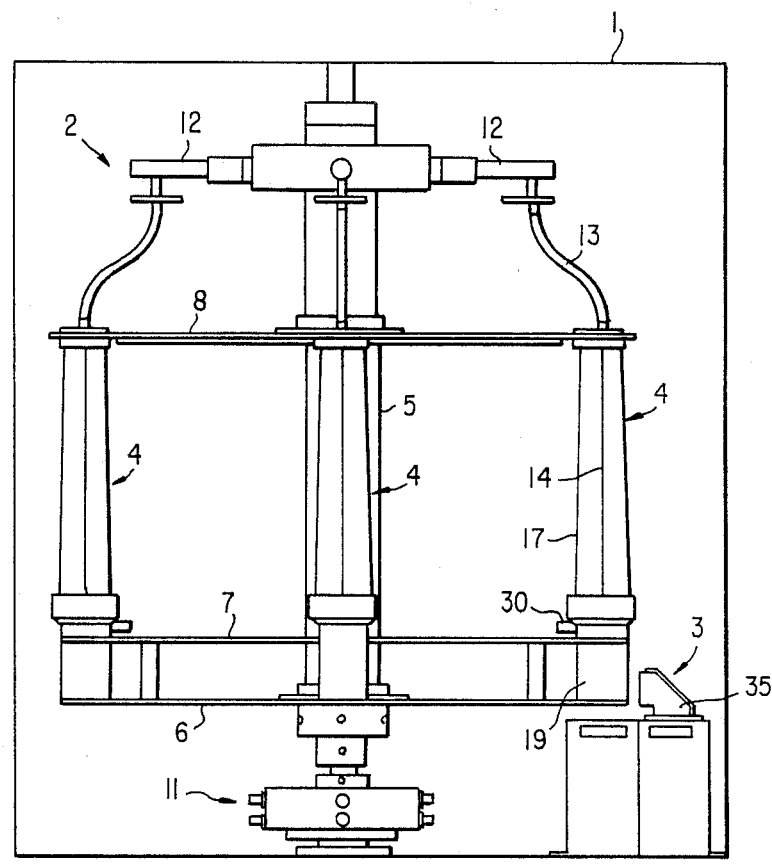
FIG. 1 is a front view of a fluorescent analysis apparatus of the present invention.

Various other objects, features and attendant advantages of the present invention will be more fully appreciated as the same becomes better understood from the following detailed description when considered in connection with the accompanying drawings in which like reference characters designate like or corresponding parts throughout the several views and wherein FIG. 1 shows the device as including an enclosure 1 which contains both the reacting board generally indicated as 2 and measuring apparatus generally indicated as 3. The enclosure 1 is a tank which is maintained at the best reaction temperature for the particular reaction involved. The temperature is maintained by a thermostatically controlled heating device (not shown). The particular best temperature depends on the particular microorganisms and enzymes present in the sample to be analyzed. Accordingly the temperature at which the enclosure is maintained should be variable over a range of values.

Figure 2:
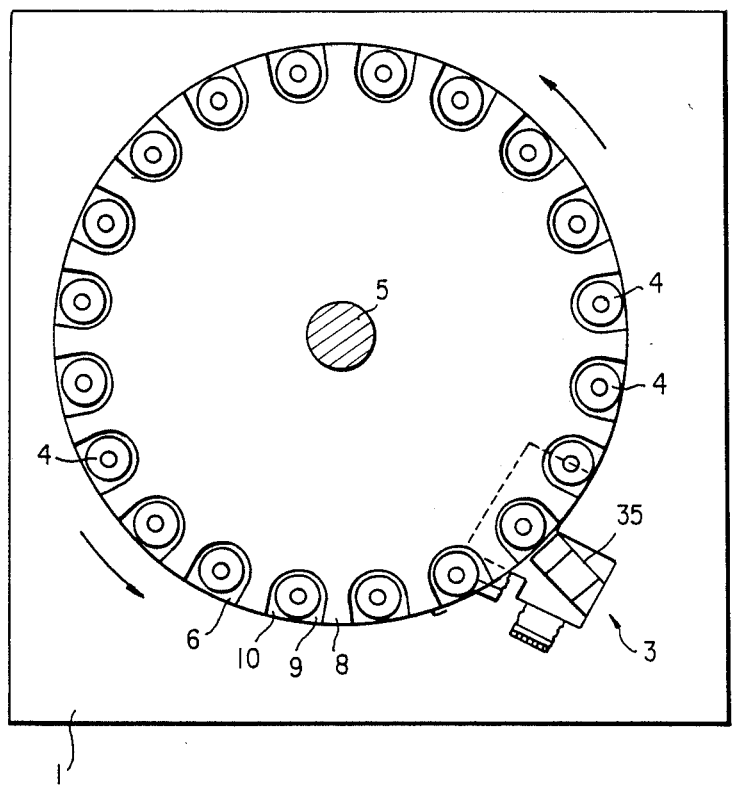
FIG. 2 is a top view of the apparatus in FIG. 1.

The reacting board is a centrally located rotatable holder for a series of reacting containers 4 which are mounted around the periphery of the board. The board is rotated by means of a motor and gearing arrangement generally indicated as 11 which turns a rotating shaft 5 in the center of the board. A base plate 6 which may be transparent, is mounted on the rotating shaft 5 and turns therewith. Also mounted on the shaft at positions above the base plate are an intermediate plate 7 and a top plate 8. The intermediate plate and top plate have concave portions 9 and 10 (see FIG. 2) at a number of locations around their periphery. A reacting container 4 may be placed on the base plate and extend upwardly through the concave portions 9 and 10 in the upper two plates. A container may be placed in each set of concave portions. By controlling the motor 11, the rotating shaft 5 may be made to drive the various reacting containers to the position in front of the measuring apparatus 3. This location is the measuring section and is the space for measuring the fluorescent substance in the reacting container. The measuring section is made so that a measurement may be made of any fluorescent substance by applying a fluorescent exciting ray and receiving a result according to the particular make up of the reaction involved.

The other positions of the reacting board away from the measurement section may be utilized as a reacting section. In this section a reactive liquid with a fluorescent substrate is applied to a sample in the reacting container 4. The reactive liquid and the sample are mixed. Any substance with an ingredient which forms fluorescent substances in response to a fluorescent substrate can be used for measuring samples. Examples of these are foods, cosmetics, pharmaceuticals, etc. Factors forming fluorescent substances in response to the fluorescent substrate include microorganisms such as bacteria, mold, yeast, and various enzymes. All substances forming fluorescent substances with enzymes may be employed as fluorescent substrates.

For example, when a sample contains micro-organisms, 4-methylumbelliferil phosphate is used as a fluorescent substrate and the fluorescent substance formed is 4-methyl-umbelliferone (4MU). In the case of a sample including peptidase, arginyl MCA or leucil MCA is used as a fluorescent substrate and the formed fluorescent substance is methylcoumarin (MCA).

Figure 3:
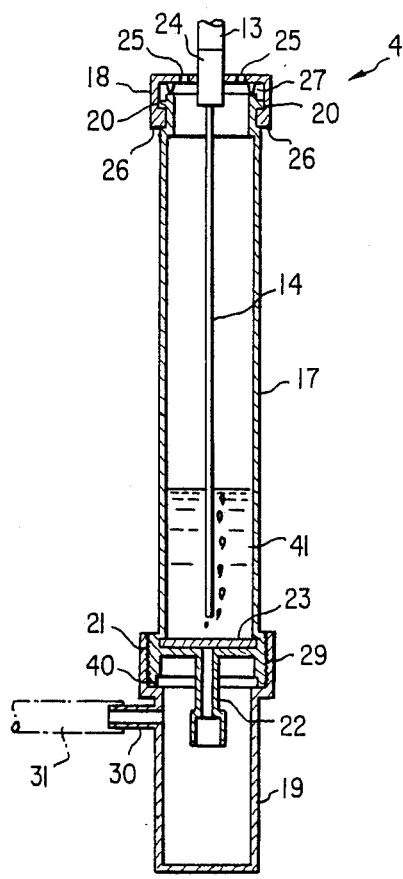
FIG. 3 is a vertical cross sectional view of the reacting container 4 shown in FIG. 1.

Fixed tubes 12 are provided around the rotating shaft and extend radially outwardly therefrom. One tube is provided for each reacting container and thus are provided at positions corresponding to concave portions 9 and 10. The tubes are preferably located above the top plate and thus above the reacting containers 4. The flexible coupling tube 13 is connected to each fixed tube and extends downwardly to a nozzle 14 which is contained within each reacting container. The ends of the fixed tubes 12 are connected to a supply of compressed air (not shown) by way of channels in the rotating shaft 5. Thus, compressed air travels through the channels, fixed tubes 12, flexible coupling tubes 13 and nozzle 14. As seen in FIG. 3, the lower end of the nozzle is open so that air is bubbled through the solution in the reacting container 4.

As further seen in FIG. 3 the reacting container is made of a reacting tube 17, a cover 18 and a measuring tube 19. The measuring tube 19 and reacting tube 17 are screwed together using interacting screw threads 21 and 29 and gasket 40. Cover 18 carries coincident L-shaped pieces 26 made on the opposite lower parts of the inner boundary thereof. Likewise, the reacting tube 30 carries coincident L-shaped pieces 20 on the periphery of the upper end which is aligned with coincident pieces 26 to seal and fix the cover 18 to the reacting tube 17 using a gasket 27.

A nozzle hole 24 is drilled into the center of cover 18 and is used for inserting and fixing the nozzle 14 and joining the nozzle to flexible coupling tube 13. A purge hole 25 is also drilled in the cover in order to allow air to escape from the reacting tube.

The measuring tube is approximately cylindrical in shape as is the reacting tube 17. Cover 18, reacting tube 17 and measuring tube 19 are all transparent synthetic resin or glass.

The bottom of reacting tube 17 is formed by horizontal surface to which a filling tube 22 projects downwardly, thus providing an exit for liquid in the reacting tube. This bottom surface is covered by a filter plate 23 which is fixed to the upper surface of the filling tube 22. Thus, in order for liquid to pass through the filling tube 22, it is necessary for it to pass through filter 23.

An air tube 30 projects from the side wall of measuring tube 19 in the direction of the rotating shaft 5. This air tube is connected to an air suction and exhaust unit (not illustrated) by way of a coupling tube 31 and channels formed in the rotating shaft 5. If desired, the connection to the suction source may only occur at certain positions along the circular travel of the apparatus such as only at the measuring station.

Figure 4:
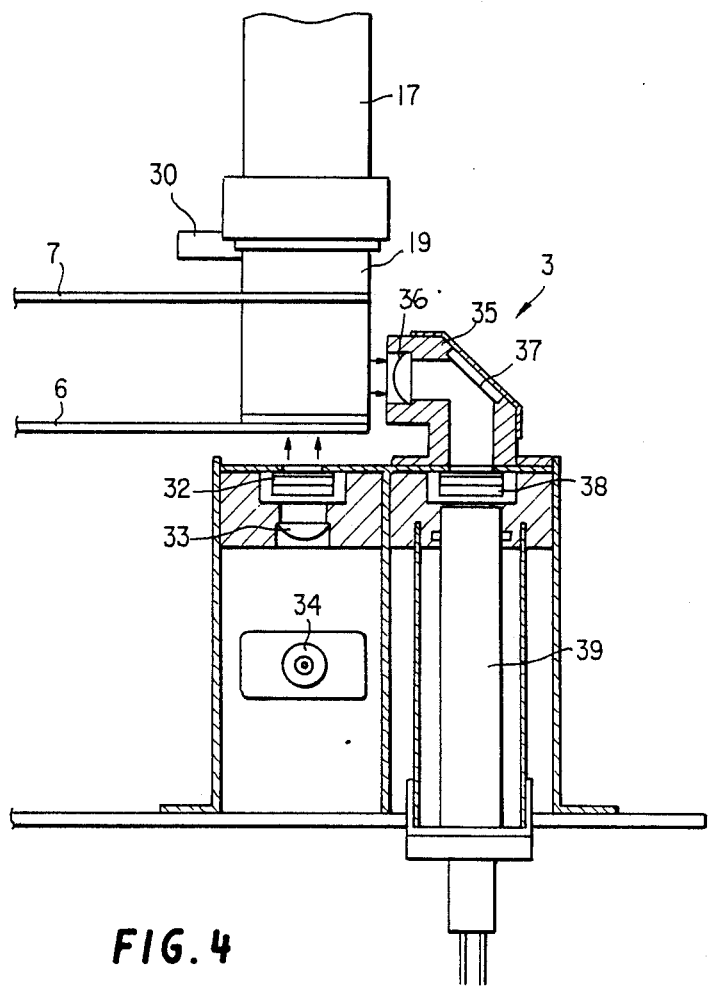
FIG. 4 is an enlarged front view of the measuring apparatus.

FIG. 4 shows a reacting container in position at the measuring section. The measuring apparatus 3 is placed so as to be below the base plate and also just outside the outer periphery of this base plate. A light source 34 provides a light beam which is focused by lens 33 and passes through an exciting ray filter 32 which allows rays of a specific wavelength, such as 360 nm to pass into the bottom of the measuring tube 19. An angled frame 35 is placed adjacent and radially outside of the measuring tube. Fluorescent rays which originate within the measuring tube pass through the transparent wall of the measuring tube and are focussed by lens 36 onto a fixed reflector 37 and through a fluorescent filter 38 which only allows light of a certain wavelength, for example 450 nm to pass. A light receiving unit 39 receives this light and measures the amount of light in a known manner in order to determine the presence of microorganism in the sample. The result of the measurement is passed through cables extending through the thermostatically controlled housing to a cathode ray tube display (not shown) or other indicator which is installed outside of the housing.

In operation, the reacting container 4 with the cover 18 removed is used to mix a sample, for example of soup and a reactive liquid, for example of $10^{-3}$ mole of 4-methylumbelliferil phosphate. Since the filter 23 blocks the passage of the liquid, the liquid stays in the reacting tube 17. The cover 18 may then be placed over the reacting tube and the entire reacting container attached to the reacting board 2. Air tube 30 is connected to the connecting tube 31 and nozzle 14 is connected to flexible coupling tube 13 through the nozzle hole 24. The thermostatically controlled enclosure automatically controls the temperature of the apparatus to be about 40° C. or other desired temperature during the remainder of the measuring cycle.

Of course, at the same time other samples may also be prepared in other reacting containers and placed on the reaction board in a similar fashion. It is also possible to insert and remove other reacting containers during the course of the reaction time.

The reaction occurs for about 2 hours in the reactive container 4 while air is supplied through a nozzle 14. The air acts to keep the liquid stirred up. When the reaction time is complete the air supply is halted and rotating shaft 5 is rotated so that the particular reacting container of interest is placed at the measuring section 3. When in position, air is sucked from the air tube 30 and connecting tube 31, causing a negative pressure in measuring tube 19. As a result, the liquid in the reacting tube 17 passes through filter 23 and filling tube 22 and is received in the measuring tube 19.

The liquid is then irradiated by 360 nm rays passing from the light source 34, lens 33 and filter 32 into the bottom of the measuring tube 19. The fluorescent rays emitted from the fluorescent substance in the measuring liquid are concentrated on the receiving unit 39 by lens 36 and reflector 37. Light of other wavelengths are removed using filter 38. The amount of incident light of the desired wavelength is measured and displayed. These measurements reveal the fluorescent substance concentration in the measuring liquid and the presence or absence of microorganisms in the sample and their concentration.

Thus, by placing both the reacting section and the measuring section of the device in a thermostatically controlled enclosure the present invention allows the continuous reaction testing of a sample with a reactive liquid and the measurement of the resultant fluorescent substance concentration without removing the reacting container. As a result the analysis may be done easily on a large number of samples without any unnecessary movements on the part of the operator. As can be easily seen, the device may also be automated since it is only necessary to sequentially perform the operation on the various reacting containers by moving the containers using motor 11.

Obviously, numerous modifications and variations of the present invention are possible in light of the above teachings. It is therefore to be understood that within the scope of the appended claims, the invention may be practiced otherwise than as specifically described herein.

What is claimed is:

1. A fluorescent analysis apparatus comprising:
a thermostatically controlled enclosure;
a reacting board contained within said enclosure, including a reacting section and a measuring section;
a plurality of containers arranged on said reacting board for receiving samples, each container having an upper part, a lower part and a filter therebetween; and
a measuring apparatus contained within the enclosure and next to the measuring section of the reacting board;
wherein a reaction involving a sample may be made in the reaction section of the reacting board and then moved to the measuring section so that a measurement may be made by the measurement apparatus without removing the sample from the enclosure.

2. The apparatus according to claim 1, wherein the containers are arranged around the periphery of a circle within the reacting board.

3. The apparatus according to claim 1, wherein a liquid is pulled from the upper container to the lower container through the filter by means of a negative pressure.

4. The apparatus according to claim 3, wherein the negative pressure is provided from a central location.

5. The apparatus according to claim 1, wherein air is bubbled to the upper part of each container during the reaction.

6. The apparatus according to claim 5, wherein the air is provided from a central location.

7. The apparatus according to claim 1, further comprising a motor drive for rotating the reacting board so as to move the containers from the reacting section to the measuring section.

8. The apparatus according to claim 1, wherein the measuring apparatus comprises a light source and filter for providing activating light of a specific wavelength.

9. The apparatus according to claim 7, wherein the measuring apparatus further comprises a filter which receives light from the sample and passes only light of a predetermined wavelength.

* * * * *